United States Patent
Frison et al.

(10) Patent No.: US 12,329,778 B2
(45) Date of Patent: Jun. 17, 2025

(54) PARTICLES OF A MIXTURE OF IRON(III)-OXYHYDROXIDE, SUCROSE AND ONE OR MORE STARCHES, PREFERABLY OF SUCROFERRIC OXYHYDROXIDE

(71) Applicant: Vifor Fresenius Medical Care Renal Pharma LTD, St. Gallen (CH)

(72) Inventors: Nicolas Frison, Mannens (CH); Miriam Spichiger, Heimisbach (CH); Mélanie Ittel, Saint-Louis (FR)

(73) Assignee: VIFOR FRESENIUS MEDICAL CARE RENAL PHARMA LTD, St. Gallen (CH)

( * ) Notice: Subject to any disclaimer, the term of this patent is extended or adjusted under 35 U.S.C. 154(b) by 0 days.

(21) Appl. No.: 17/310,351

(22) PCT Filed: Jan. 14, 2021

(86) PCT No.: PCT/EP2021/050697
§ 371 (c)(1),
(2) Date: Jul. 28, 2021

(87) PCT Pub. No.: WO2021/144364
PCT Pub. Date: Jul. 22, 2021

(65) Prior Publication Data
US 2022/0370494 A1    Nov. 24, 2022

(30) Foreign Application Priority Data

Jan. 16, 2020   (EP) .................................. 20152163

(51) Int. Cl.
*A61K 33/26*    (2006.01)
*A61K 9/16*     (2006.01)
*A61K 9/20*     (2006.01)

(52) U.S. Cl.
CPC ............ *A61K 33/26* (2013.01); *A61K 9/1623* (2013.01); *A61K 9/1652* (2013.01); *A61K 9/2018* (2013.01); *A61K 9/2059* (2013.01)

(58) Field of Classification Search
CPC .... A61K 33/26; A61K 9/1623; A61K 9/1652; A61K 9/2018; A61K 9/2059
See application file for complete search history.

(56) References Cited

U.S. PATENT DOCUMENTS

| 5,514,281 | A  | 5/1996 | Boos et al. |
| 6,117,451 | A  | 9/2000 | Kumar |
| 6,174,442 | B1 | 1/2001 | Geisser et al. |
| 2002/0044969 | A1 | 4/2002 | Harden et al. |
| 2008/0145410 | A1 | 6/2008 | Ambuhl et al. |
| 2009/0317459 | A1 | 12/2009 | Pennel et al. |
| 2010/0247609 | A1 | 9/2010 | Weibel et al. |
| 2012/0201864 | A1 | 8/2012 | Applewhite et al. |

FOREIGN PATENT DOCUMENTS

| GB | 1249558 | 10/1971 | |
| WO | WO 02/13793 | 2/2002 | |
| WO | WO 2008/071747 | 6/2008 | |
| WO | WO-2008071747 A1 * | 6/2008 | ............. A61K 33/26 |
| WO | WO-2009062993 A1 * | 5/2009 | ............. A61K 33/26 |
| WO | WO 2010/015827 | 2/2010 | |
| WO | WO 2015/078900 | 6/2015 | |
| WO | WO-2015078900 A1 * | 6/2015 | ............. A61K 33/26 |

OTHER PUBLICATIONS

Kornblum, "Sustained-Action Tablets Prepared by Employing a Spray-Drying Technique for Granulation," Journal f Pharmaceutical Science, 1969, 58(1):125-127.
Lanz et al., "Chewability testing in the development of a chewable tablet for hyperphosphatemia," Drug Dev Ind Pharm. Dec. 2014 40(12):1623-1631.
Livingstone, "Pharmaceutics: The Science of Dosage Form Design," 2002, 2nd Edition, edited by M.E. Aulton, pp. 389, 390 & 12 (ISBN O 3 05517 5).
McCormick, "Evolutions in Direct Compression," Pharmaceutical Technology, Apr. 2005, pp. 52-62.
Mendes et al., "Chewable Tables" in Pharmaceutical Dosage Forms: Tablets, Marcel Dekker, inc., 1989, $2^{nd}$ Edition, edited by H.A. Lieberman, L. Lachman, and J.B. Schwartz, pp. 367-417.
Mohan, "Compression physics of pharmaceutical powders: A review," IJPSR, 2012, vol. 3(6): 1580-1592.
Remington, "Pharmaceutical Sciences," Mack Printing Co, $16^{th}$ edition, 1980, pp. 1553-1576.
Remington, "The Science and Practice of Pharmacy," Mack Printing Co., $19^{th}$ edition, vol. 11, 1995, pp. 1616-1620 and 1627-1628.
Shangraw, "Compressed Tablets by Direct Compression," in 1 Pharmaceutical Dosage Forms: Tablets, vol. 1, 195 (Herbert A. Lieberman et al., 2d ed. 1989), pp. 195-26.
Tousey, "Optimal Tablet Press Operation Machine versus Granulation," Pharmaceutical Technology, Jan. 2002, pp. 52-60.
Yajima et al., "Optimization of Size Distribution of Granules for Tablet Compression," Chem. Pharm. Bull., 1996, 44(5), pp. 1056-1060.
International Search Report dated Apr. 21, 2021 for International Application No. PCT/EP2021/050697.

* cited by examiner

*Primary Examiner* — Robert A Wax
*Assistant Examiner* — John W Lippert, III
(74) *Attorney, Agent, or Firm* — Finnegan, Henderson, Farabow, Garrett & Dunner LLP

(57) ABSTRACT

The invention relates to particles of a mixture of iron(III)-oxyhydroxide, sucrose and one or more starches, preferably of sucroferric oxyhydroxide having a certain particle size distribution, a process for the manufacture thereof, the pharmaceutical composition comprising the same, in particular compressed tablets.

41 Claims, 2 Drawing Sheets

PARTICLES OF A MIXTURE OF IRON(III)-OXYHYDROXIDE, SUCROSE AND ONE OR MORE STARCHES, PREFERABLY OF SUCROFERRIC OXYHYDROXIDE

Sucroferric oxyhydroxide is a phosphate adsorbent that is currently marketed as a chewable tablet under the tradename Velphoro®. WO2009/062993 A1 describes pharmaceutical compositions comprising iron oxy-hydroxide in high loading, in a form suitable for oral administration. WO2015/078900 describes pharmaceutical compositions, comprising a phosphate binder, in particular, sucroferric oxyhydroxide, where the phosphate binder particles having a certain particle size distribution with a d50 is in the range of 30 to 120 μm. The sucroferric oxyhydroxide described therein is obtained by a spray drying process, which is then formulated with further excipients to a powder that is pressed into chewable tablets comprising 2500 mg sucroferric oxyhydroxide corresponding to about 500 mg iron. For certain applications, in particular, pediatric applications, or for patients with dysphagia, a chewable tablet of this size is not desirable. The inventors therefore looked for different dosage forms. When they tried to form smaller tablets, such as micro-tablets, which generally have diameters between 1 to 4 mm, the inventors were faced with unexpected problems. Obviously due to higher ejection forces in micro-tableting tools they found that the use of the known sucroferric oxyhydroxide compositions lead to dark brown marks on the extremities of the micro-tablets. The inventors, therefore, were looking for ways to solve this problem. Surprisingly they found that when the known sucroferric oxyhydroxide particles obtained by spray drying were subjected to agglomeration leading to a decrease of smaller particles and an increase of bigger particles, that the use of such agglomerated sucroferric oxyhydroxide particles in tableting allows also for the manufacture of suitable smaller tablets, in particular, micro- or mini-tablets.

Figure 1:
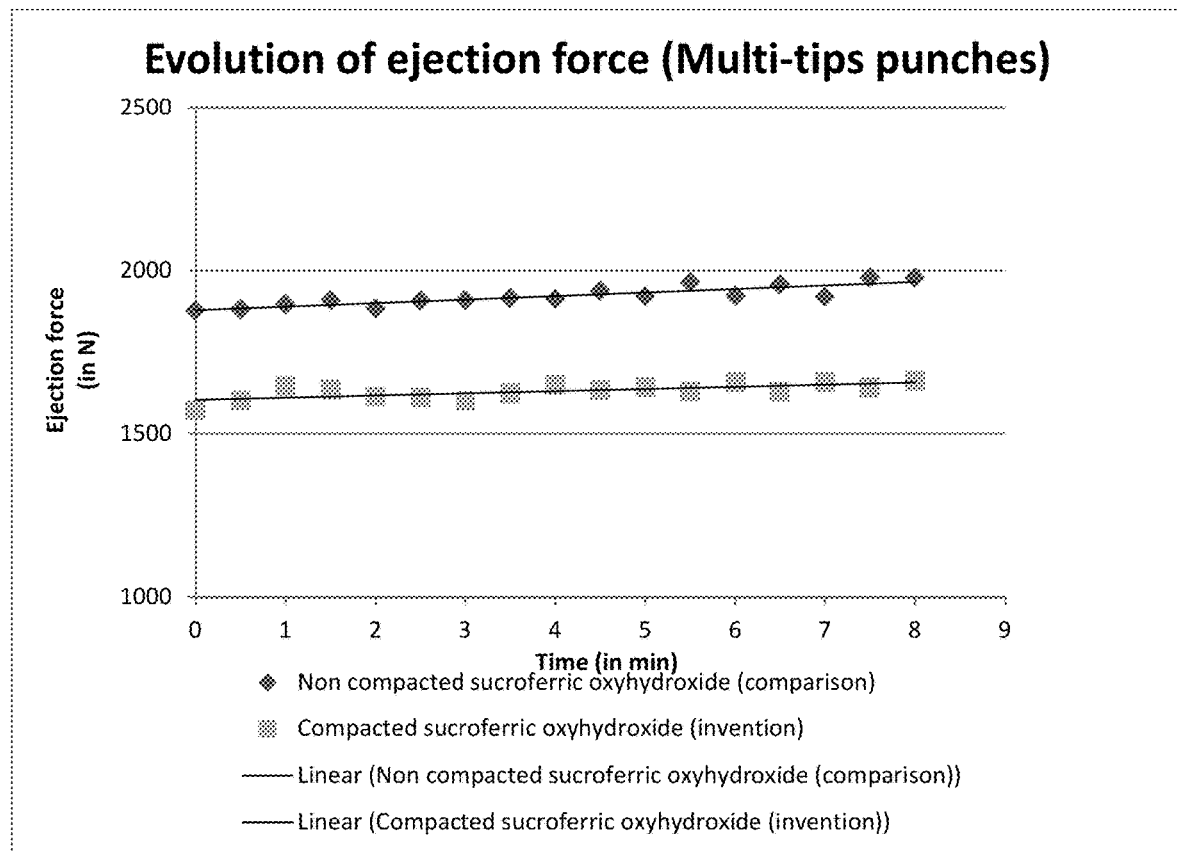
FIG. 1 depicts the results on the evolution of the ejection forces during tableting for each of a non-compacted sucroferric oxyhydroxide composition according to Comparative Example 1 and a compacted sucroferric oxyhydroxide composition according to Example 1.

Accordingly, the present invention provides particles, comprising iron(III)-oxyhydroxide, sucrose and one or more starches, preferably particles of sucroferric oxyhydroxide, wherein the fraction of particles with a particle sizes of above 90 μm is 25 weight % or more, preferably 35 weight % or more, more preferably 40 weight % or more, even more preferably 45 weight % or more, and most preferably 50 weight % or more, and wherein preferably the fraction of particles with a particle size of above 125 μm is 25 weight % or more, preferably 30 weight % or more, and more preferably 35 weight % or more, each based on the total weight of the particles, as determined by sieve analysis. The sieve analysis is in particular carried out based on the European Pharmacopeia 2.9.38 particle-size distribution estimation by analytical sieving, preferably according to the following method of determination:

Sieving method=mechanical vibration (vibratory sieve shaker e.g. Retsch AS200)

Sample size=100 g

Column of sieves=0 (bottom plate), 90, 125, 180, 250, 355, 500 and 710 microns

Amplitude level=1.5

Duration=10 minutes.

Preferably the fraction of particles with a particle size in the range of 90 μm to 125 μm is 3 weight % or more,
more preferably 4 weight % or more,
still more preferably 5 weight % or more,
each based on the total weight of the particles, as determined by sieve analysis.

Preferably the fraction of particles with a particle size in the range of 90 μm to 125 μm is at most 20 weight %,
more preferably at most 15 weight %,
still more preferably at most 10 weight %,
each based on the total weight of the particles, as determined by sieve analysis.

Preferably the fraction of particles with a particle size in the range of 90 μm to 125 μm is in the range of
3 weight % to 20 weight %,
more preferably in the range of 4 weight % to 15 weight %,
still more preferably in the range of 5 weight % to 10 weight %,
each based on the total weight of the particles, as determined by sieve analysis.

Preferably the fraction of particles with a particle size in the range of 125 μm to 180 μm is
3 weight % or more,
preferably 4 weight % or more,
more preferably 5 weight % or more,
each based on the total weight of the particles, as determined by sieve analysis.

Preferably the fraction of particles with a particle size in the range of 125 μm to 180 μm is
at most 20 weight %,
more preferably at most 15 weight %,
still more preferably at most 12 weight %, Preferably the fraction of particles with a particle size in the range of 125 μm to 180 μm is in the range of
3 weight % to 20 weight %,
more preferably in the range of 4 weight % to 15 weight %,
still more preferably in the range of 5 weight % to 12 weight %,
each based on the total weight of the particles, as determined by sieve analysis.

Preferably the fraction of particles with a particle size in the range of 180 μm to 250 μm is
3 weight % or more,
preferably 4 weight % or more,
more preferably 5 weight % or more,
each based on the total weight of the particles, as determined by sieve analysis.

Preferably the fraction of particles with a particle size in the range of 180 μm to 250 μm is
at most 20 weight %,
more preferably at most 15 weight %,
still more preferably at most 10 weight %,
each based on the total weight of the particles, as determined by sieve analysis.

Preferably the fraction of particles with a particle size in the range of 180 μm to 250 μm is in the range of
3 weight % to 20 weight %,
more preferably in the range of 4 weight % to 15 weight %, still more preferably in the range of 5 weight % to 10 weight %,
each based on the total weight of the particles, as determined by sieve analysis.

Preferably the fraction of particles with a particle size in the range of 250 µm to 355 µm is
3 weight % or more,
preferably 4 weight % or more,
more preferably 5 weight % or more,
each based on the total weight of the particles, as determined by sieve analysis.

Preferably the fraction of particles with a particle size in the range of 250 µm to 355 µm is
at most 20 weight %,
more preferably at most 16 weight %,
still more preferably at most 13 weight %,
each based on the total weight of the particles, as determined by sieve analysis.

Preferably the fraction of particles with a particle size in the range of 250 µm to 355 µm is in the range of
3 weight % to 20 weight %,
more preferably in the range of 4 weight % to 16 weight %,
still more preferably in the range of 5 weight % to 13 weight %,
each based on the total weight of the particles, as determined by sieve analysis.

Preferably the fraction of particles with a particle size in the range of 355 µm to 500 µm is
3 weight % or more,
preferably 5 weight % or more,
more preferably 8 weight % or more,
each based on the total weight of the particles, as determined by sieve analysis.

Preferably the fraction of particles with a particle size in the range of 355 µm to 500 µm is
at most 20 weight %,
more preferably at most 18 weight %,
still more preferably at most 16 weight %,
each based on the total weight of the particles, as determined by sieve analysis.

Preferably the fraction of particles with a particle size in the range of 355 µm to 500 µm is in the range of
3 weight % to 20 weight %,
more preferably in the range of 5 weight % to 18 weight %,
still more preferably in the range of 8 weight % to 16 weight %,
each based on the total weight of the particles, as determined by sieve analysis.

Preferably the fraction of particles with a particle size in the range of 500 µm to 710 µm is
3 weight % or more,
preferably 4 weight % or more,
more preferably 5 weight % or more,
each based on the total weight of the particles, as determined by sieve analysis.

Preferably the fraction of particles with a particle size in the range of 500 µm to 710 µm is
at most 20 weight %,
more preferably at most 16 weight %,
still more preferably at most 13 weight %,
each based on the total weight of the particles, as determined by sieve analysis.

Preferably the fraction of particles with a particle size in the range of 500 µm to 710 µm is in the range of
3 weight % to 20 weight %,
more preferably in the range of 4 weight % to 16 weight %,
still more preferably in the range of 5 weight % to 13 weight %,
each based on the total weight of the particles, as determined by sieve analysis.

Preferably the fraction of particles with a particle size in the range of 90 to 710 µm is
30 weight % or more,
preferably 35 weight % or more,
more preferably 40 weight % or more,
each based on the total weight of the particles, as determined by sieve analysis.

Preferably the fraction of particles with a particle size in the range of 90 to 710 µm is at most 70 weight %
more preferably at most 60 weight %,
still more preferably at most 55 weight %,
each based on the total weight of the particles, as determined by sieve analysis.

Preferably the fraction of particles with a particle size in the range of 90 µm to 710 µm is in the range of
30 weight % to 70 weight %,
more preferably in the range of 35 weight % to 60 weight %,
still more preferably in the range of 40 weight % to 55 weight %,
each based on the total weight of the particles, as determined by sieve analysis.

Preferably,
the fraction of particles with a particle size in the range of 125 µm to 180 µm is
3 weight % or more, preferably 4 weight % or more, more preferably 5 weight % or more, and the fraction of particles with a particle size in the range of 180 µm to 250 µm is
3 weight % or more, preferably 4 weight % or more, more preferably 5 weight % or more, and the fraction of particles with a particle size in the range of 250 µm to 355 µm is
3 weight % or more, preferably 4 weight % or more, more preferably 5 weight % or more, and the fraction of particles with a particle size in the range of 355 µm to 500 µm is
3 weight % or more, preferably 5 weight % or more, more preferably 8 weight % or more, and and the fraction of particles with a particle size in the range of 500 µm to 710 µm is
3 weight % or more, preferably 4 weight % or more, more preferably 5 weight % or more,
each based on the total weight of the particles, as determined by sieve analysis.

Preferably,
the fraction of particles with a particle size in the range of 125 µm to 180 µm is
at most 20 weight %, more preferably at most 15 weight %, still more preferably at most 12 weight %, and
the fraction of particles with a particle size in the range of 180 µm to 250 µm is
at most 20 weight %, more preferably at most 15 weight %, still more preferably at most 10 weight %, and
the fraction of particles with a particle size in the range of 250 µm to 355 µm is
at most 20 weight %, more preferably at most 16 weight %, still more preferably at most 13 weight %, and
the fraction of particles with a particle size in the range of 355 µm to 500 µm is at most 20 weight %, more preferably at most 18 weight %, still more preferably at most 16 weight %, and the fraction of particles with a particle size in the range of 500 μm to 710 μm is at most 20 weight %, more preferably at most 16 weight %, still more preferably at most 13 weight %, each based on the total weight of the particles, as determined by sieve analysis.

Preferably, the fraction of particles with a particle size in the range of 125 μm to 180 μm is in the range of 3 weight % to 20 weight %, more preferably in the range of 4 weight % to 15 weight %, still more preferably in the range of 5 weight % to 12 weight %, and the fraction of particles with a particle size in the range of 180 μm to 250 μm is in the range of 3 weight % to 20 weight %, more preferably in the range of 4 weight % to 15 weight %, still more preferably in the range of 5 weight % to 10 weight %, and the fraction of particles with a particle size in the range of 250 μm to 355 μm is in the range of 3 weight % to 20 weight %, more preferably in the range of 4 weight % to 16 weight %, still more preferably in the range of 5 weight % to 13 weight %, and the fraction of particles with a particle size in the range of 355 μm to 500 μm is in the range of 3 weight % to 20 weight %, more preferably in the range of 5 weight % to 18 weight %, still more preferably in the range of 8 weight % to 16 weight %, and the fraction of particles with a particle size in the range of 500 μm to 710 μm is in the range of 3 weight % to 20 weight %, more preferably in the range of 4 weight % to 16 weight %, still more preferably in the range of 5 weight % to 13 weight %, each based on the total weight of the particles, as determined by sieve analysis.

Preferably the fraction of particles which have a particle size of >710 μm is less than 5 weight %, and preferably less than 3 weight %, based on the total weight of the particles, as determined by sieve analysis.

Preferably the particles, comprising iron(III)-oxyhydroxide, sucrose and one or more starches, consists of iron(III)-oxyhydroxide, sucrose, one or more starches and optionally residual water. More preferably the particles, comprising iron(III)-oxyhydroxide, sucrose and one or more starches, are particles of sucroferric oxyhydroxide. "Sucroferric oxyhydroxide" (NONPROPRIETARY NAME ADOPTED BY THE USAN (United States Adopted Names) COUNCIL) is a mixture of iron(III)-oxyhydroxide, sucrose, and starches. As described in WO2015/078900 sucroferric oxyhydroxide is a stabilized polynuclear iron(III)-oxyhydroxide, which can be obtained in particular by precipitation of polynuclear iron(III)-oxyhydroxide from an iron(III)-chloride solution with sodium carbonate, subsequent addition of sucrose and starches and subjecting the suspension to spray drying. Such process leads to particles of sucroferric oxyhydroxide which generally have more than about 80 weight % of particles of less than 90 μm, that is, the fraction of coarser particles of more than 90 μm is generally about 20 weight % or less, although it is also possible to obtain the claimed coarser particles directly from the spray-drying process, by applying suitable spray-drying conditions. In accordance with the present invention the particles comprising iron(III)-oxyhydroxide, sucrose and one or more starches, preferably particles of sucroferric oxyhydroxide, however, are preferably subjected to an agglomeration or granulation process as described below leading to a coarser particle size distribution, which is characterized by having the fraction of particles with a particle size of above 90 μm of 25 weight % or more preferably 35 weight % or more, more preferably 40 weight % or more, even more preferably 45 weight % or more, and most preferably 50 weight % or more, and by having the fraction of particles with a particle size of above 125 μm of 25 weight % or more, preferably 30 weight % or more, and more preferably 35 weight % or more, each based on the total weight of the particles, as determined by sieve analysis as mentioned above. Such particles can be compressed optionally after admixture with very low amounts of one or more excipients to micro- or mini-tablets without the formation of marks on the extremities of the micro- or mini-tablets and with a high load of, in particular, sucroferric oxyhydroxide.

The term "starch" as used herein includes any conventionally used starch products (such as potato starch, corn starch, rice starch, tapioca starch) in native, pregelatinized, degraded, modified, and derivatized forms, preferably suitable for direct compression, and mixtures thereof. Most preferred products include native and pregelatinized starch, such as, in particular, a mixture having a weight ratio (native-pregelatinized) in the weight-range of 10:1 to 0.5:1, preferably in the range of 3:1 to 0.5:1, more preferably in the range of 2:1 to 1:1, still more preferably about 2:1. Most preferably a mixture of potato starch and pregelatinized starch in a weight ratio of about 2:1 is used.

In accordance with the present invention the particles, comprising iron(III)-oxyhydroxide, sucrose and one or more starches, in particular, the particles of sucroferric oxyhydroxide preferably comprise about 20 to about 50 weight % iron(III)-oxyhydroxide, about 20 to 50 weight % sucrose, and about 20 to 50 weight % of one or more starches, based on the total weight of the particles. More preferably the particles comprise about 20 to about 40 weight % iron(III)-oxyhydroxide, about 20 to 40 weight % sucrose, and about 20 to 40 weight % of one or more starch, based on the total weight of the particles. Still more preferably the particles comprise about 28 to about 38 weight % iron(III)-oxyhydroxide, about 25 to 35 weight % sucrose, and about 23 to 33 weight % of one or more starch, based on the total weight of the particles. In a further preferred embodiment, the particles according to the invention comprise a mixture of native and pregelatinised starch. Native starch includes for example potato starch, corn starch, rice starch, and tapioca starch, preferred is potato starch. Pregelatinised starch is suitably obtained by starch gelatinization which is a process of breaking down the intermolecular bonds of starch molecules in the presence of water and heat, allowing the hydrogen bonding sites (the hydroxyl hydrogen and oxygen) to engage more water. As explained above mixtures of native and pregelatinized starch are particularly suitable, such as, in particular, a mixture having a weight ratio (native:pregelatinized) in the weight-range of 10:1 to 0.5:1, preferably in the range of 3:1 to 0.5:1, more preferably in the range of 2:1 to 1:1 and most preferably in a weight ratio of about 2:1.

Preferably the particles according to the invention have an iron content of about 15 to about 28 weight %, preferably about 19 to about 23 weight %, based on the total weight of the particles.

The particles according to the invention may comprise water in an amount of up to about 15 weight %, preferably up to about 10 weight %, based on the total weight of the particles.

The particles according to the invention, in particular, the particles of sucroferric oxyhydroxide suitably consist of iron(III)-oxyhydroxide, sucrose, one or more starches and water.

The present invention furthermore relates to a preferred process for the manufacture of the particles according the invention, wherein particles, comprising iron(III)-oxyhydroxide, sucrose and one or more starches, preferably particles of sucroferric oxyhydroxide having a fraction of particles with particle sizes of above 90 μm of less than 25 weight % are subjected to an agglomeration or granulation process, such as a dry or wet granulation process, preferred to a dry granulation (compaction) process. In a particular preferred embodiment of the process for the manufacture according to the invention, the particles, comprising iron (III)-oxyhydroxide, sucrose and one or more starches, preferably the particles of sucroferric oxyhydroxide having a fraction of particles with particle sizes of above 90 μm of less than 25 weight % are subjected to compaction with a roller compactor. Roller compaction is preferably carried out as follows: the drug substance goes through the roller compactor with a defined roller gap and hydraulic pressure to obtain ribbons which are broken with a chopper and subsequently milled through a defined final mesh screen size. As mentioned above, alternatively the particles according the invention may be also directly obtained by the spray-drying process by suitably adjusting the spray-drying conditions.

The particles, comprising iron(III)-oxyhydroxide, sucrose and one or more starches, preferably the particles of sucroferric oxyhydroxide having a fraction of particles with particle sizes of above 90 μm of less than 25 weight % used as a starting material for the agglomeration process are preferably obtained by spray-drying of an aqueous suspension comprising iron(III)-oxyhydroxide, sucrose and one or more starches as mentioned above. Preferably the aqueous suspension comprising iron(III)-oxyhydroxide, sucrose and one or more starches, preferably comprising sucroferric oxyhydroxide is subjected to atomization prior to spray-drying. Atomization of the feed might be generally achieved by basic feed devices of the single fluid nozzle or pressure type, of the two-fluid nozzle or pneumatic type, and of the centrifugal (spinning disc) type. In the present invention atomization is preferably done with the centrifugal (spinning disc) type atomizer. Centrifugal atomization achieves dispersion by centrifugal force, with the feed liquor being pumped to a spinning disc. In the present invention in particular spray drying on an Anhydro Spray drying plant type CSD No. 73 was found to result in an appropriate drying process. For the atomization of the concentrated aqueous PA21 suspension a centrifugal atomizer CE 250 can be used, that atomizes by feeding the liquid feed onto a high-speed wheel. With a rotary atomizer, it is possible to adjust the wheel speed and thereby the particle size better than with a nozzle. Further, rotary atomization is better suited for a shorter spray dryer. The powder received from the spray drying process should have a good flowability and the particle size of the dried product should not be too small. With the rotary atomizer, the particle size can be adjusted in particular by variation of the wheel speed. The wheel speed of the atomizer defines the size of the drops which fall into the drying chamber of the spray dryer. The size of the drops influences the particle size of the dried powder as well as its loss on drying. A higher wheel speed produces smaller drops resulting in a smaller particle size of the dried powder and a lower loss on drying, because a smaller drop contains less water which is faster vaporized during its way through the drying chamber. Since the correlation between the wheel speed and the particle size depends on the chamber geometry, it has to be adapted for each individual plant. For the geometry of the preferred Anhydro Spray drying plant type CSD No. 73 used a wheel speed of between 12000 and 20000 rpm, was found to be suitable for achieving desired particle size distribution. The inlet temperature of the air defines the drying energy which is brought into the spray dryer. Together with the inlet gas flow it defines the drying capacity. The inlet gas flow was kept constant at about $1.9\times10^4$ $m^3/h$. The inlet temperature was found suitable in the range of 130-180° C. for the Anhydro Spray drying plant type CSD No. 73.

The present invention further relates to the use of particles, comprising iron(III)-oxyhydroxide, sucrose and one or more starches, preferably the use of particles of sucroferric oxyhydroxide having the fraction of particles with a particle sizes of above 90 μm of 25 weight % or more, preferably 35 weight % or more, more preferably 40 weight % or more, even more preferably 45 weight % or more, and most preferably 50 weight % or more, and having the fraction of particles with a particle size of above 125 μm of 25 weight % or more, preferably 30 weight % or more, and more preferably 35 weight % or more, each based on the total weight of the particles, as determined by sieve analysis, for the manufacture of a pharmaceutical composition, and thus relates also to pharmaceutical compositions, comprising the particles, comprising iron(III)-oxyhydroxide, sucrose and one or more starches, preferably particles of sucroferric oxyhydroxide having the fraction of particles with a particle sizes of above 90 μm of 25 weight % or more, preferably 35 weight % or more, more preferably 40 weight % or more, even more preferably 45 weight % or more, and most preferably 50 weight % or more, and having the fraction of particles with a particle size of above 125 μm of 25 weight % or more, preferably 30 weight % or more, and more preferably 35 weight % or more, each based on the total weight of the particles, as determined by sieve analysis. A particular preferred embodiment relates to a compressed pharmaceutical composition, obtainable by compressing a pharmaceutical composition, comprising particles, comprising iron(III)-oxyhydroxide, sucrose and one or more starches, preferably particles of sucroferric oxyhydroxide having a fraction of particles with a particle sizes of above 90 μm of 25 weight % or more, preferably 35 weight % or more, more preferably 40 weight % or more, even more preferably 45 weight % or more, and most preferably 50 weight % or more, and having the fraction of particles with a particle size of above 125 μm of 25 weight % or more, preferably 30 weight % or more, and more preferably 35 weight % or more, each based on the total weight of the particles, as determined by sieve analysis. The compressed pharmaceutical composition according to the invention is preferably selected from a tablet, in particular, a mini- or micro-tablet, which usually have diameters between one to four millimeters. For example, for a cylindrical shape, the diameter is usually the diameter of the base area of the cylinder, and for a spherical shape the diameter is usually the diameter of the sphere.

In a preferred embodiment of the present invention the pharmaceutical composition comprises at least about 90 wt-%, preferably at least about 95 weight %, still more preferably at least about 97 weight % of the total of iron(III)-oxyhydroxide, sucrose and one or more starches, preferably of the sucroferric oxyhydroxide based on the total weight of the pharmaceutical composition.

The pharmaceutical composition according to the invention, preferably comprises iron(III)-oxyhydroxide, sucrose and one or more starches, preferably sucroferric oxyhydroxide and one or more excipients, such as fillers, binders, diluents, lubricants, disintegrants, glidants, disintegrants, coloring agents, flavors, sweeteners, sorbents, stabilizers, surfactants, coating materials or plasticizers.

The excipients are typically used in an amount of for example 0.01% to 10% or 0.01% to 6% or 0.1% to 6% (by weight on a dry weight basis). Preferably additional excipients are only those selected from flavor, sweeteners or taste-enhancing agents, glidants or lubricants, the latter being preferably selected from magnesium stearate or collodial silicas like Aerosil®, which are used in an amount of at most 10%, preferably at most 6%, more preferably at most 3% (by weight on a dry weight basis).

In a preferred embodiment, the pharmaceutical composition according to invention comprises at least one lubricant preferably magnesium stearate and a flavor agent. One, two, three or more diluents or fillers can be selected as further pharmaceutically acceptable excipient. Examples of pharmaceutically acceptable fillers and pharmaceutically acceptable diluents include, but are not limited to, e.g. confectioner's sugar, compressible sugar, dextran, dextrin, dextrose, lactose, mannitol, microcrystalline cellulose, powdered cellulose, sorbitol, sucrose and talc. The preferred diluents include e.g. microcrystalline cellulose. Microcrystalline cellulose is available from several suppliers. Suitable microcrystalline cellulose includes Avicel products, manufactured by FMC Corporation. Another diluent is e.g. lactose. The diluent, fillers, e.g., may be present in an amount from about 0.1% to 20% and about 0.5%-40% respectively by weight of the composition. One, two, three or more disintegrants can be selected. Examples of pharmaceutically acceptable disintegrants include, but are not limited to, e.g. starches; clays; celluloses; alginates; gums; cross-linked polymers, e.g., cross-linked polyvinyl pyrrolidone, cross-linked calcium carboxymethylcellulose and cross-linked sodium carboxymethylcellulose; soy polysaccharides; and guar gum. The disintegrant, e.g., may be present in an amount from about 0.01% to about 10% by weight of the composition. A disintegrant is also an optional but useful component of the tablet formulation. Disintegrants are included to ensure that the tablet has an acceptable rate of disintegration. Typical disintegrants include starch derivatives and salts of carboxymethylcellulose. Sodium starch glycolate is the preferred disintegrant for this formulation. One, two, three or more lubricants can be selected. Examples of pharmaceutically acceptable lubricants and pharmaceutically acceptable glidants include, but are not limited to, e.g. colloidal silica, magnesium trisilicate, talc, tribasic calcium phosphate, magnesium stearate, aluminum stearate, calcium stearate, stearic acid, polyethylene glycol and glycerol behenate. The lubricant, e.g., may be present in an amount from about 0.01 to 10% or from 0.1% to about 6% by weight of the composition; whereas, the glidant, e.g., may be present in an amount from about 0.01 to 10% or about from 0.1% to about 10% by weight. Lubricants are typically added to prevent the tablet blend from sticking to punches, minimize friction during tablet compression and allow for removal of the compressed tablet from the die. Such lubricants are commonly included in the final tablet mix in amounts usually around or less than 2% by weight. The lubricant component may be hydrophobic or hydrophilic. Examples of such lubricants include e.g. stearic acid, talc and magnesium stearate. Magnesium stearate reduces the friction between the die wall and tablet mix during the compression and ejection of the tablets. It helps prevent adhesion of tablets to the punches and dies. Magnesium stearate also aids in the flow of the powder in the hopper and into the die. The preferred lubricant, magnesium stearate is also employed in the formulation. Preferably, the lubricant is present in the tablet formulation in an amount of from about 0.01 to 10% or from about 0.1% to about 6%; also preferred is a level of about 0.1% to about 4% by weight; and most preferably from about 0.1% to about 2% by weight of the composition. Other possible lubricants include talc, polyethylene glycol, silica and hardened vegetable oils. In an optional embodiment of the invention, the lubricant is not present in the formulation, but is sprayed onto the dies or the punches rather than being added directly to the formulation. Conventional solid fillers or carriers are substances such as, e.g. calcium phosphate, calcium sulfate, calcium stearate, glyceryl mono- and distearate, sorbitol, mannitol, gelatin, natural or synthetic gums, such as carboxymethyl cellulose, methyl cellulose, alginate, dextran, acacia gum, karaya gum, locust bean gum, tragacanth and the like, diluents, binders, disintegrating agent, coloring and flavoring agents could optionally be employed. Binders are agents, which impart cohesive qualities to the powdered material. Examples of pharmaceutically acceptable binders as excipients include, but are not limited to, starches, sugars; celluloses and derivatives thereof, e.g., microcrystalline cellulose, hydroxypropyl cellulose, hydroxylethyl cellulose and hydroxylpropylmethyl cellulose; sucrose; glucose, dextrose, lactose dextrose; corn syrup; polysaccharides; and gelatin. During the clinical trials, the applicant has furthermore realized that the taste of the phosphate binder was not appreciated by the subjects and did directly affect the compliance with the therapeutic treatment (treatment adherence). For sake of clarity it should be noted that sucrose and starches being part of the active ingredient comprising iron(III)-oxyhydroxide, sucrose and one or more starches, in particular, the sucroferric oxyhydroxide do not count as excipients, like binders, sweeteners, etc. listed here. In a further embodiment the pharmaceutical composition of the invention comprises one or more flavoring or taste-masking and coloring additives such as e.g., flavours, sweeteners, taste-enhancing agents, colorants, and the like, which are typically used for oral dosage forms. In a preferred embodiment the formulations, compositions and tablets of the invention comprise a flavouring agent with Woodberry flavour. The Woodberry flavor provides better compliance and acceptance of the claimed phosphate binder tablets. Taste-masking agents, such as a taste-enhancing agent, flavouring agent, and/or natural or artificial sweetener, including intense sweetener, may be incorporated into oral dosage forms, to give them a more pleasant taste or to mask an unpleasant one. Typical sweeteners as excipient include, but are not limited to, sugars like e.g. sucrose, fructose, lactose, confectionery sugar, powdered sugar, or are polyols which is e.g. sorbitol (e.g. Neosorb), xyitol, maltitol, maltose and polydextrose, or a mixture thereof. Typical intense sweeteners may include, but not be limited to, e.g. aspartame, sucralose, acesulfam K, and/or saccharin derivatives, or a mixture thereof. Further suitable sweeteners or taste-enhancing agents include glycosides such as e.g. neohesperidin dihydrochalcone (neohesperidin DC or NHDC), glycyrrhizin, glutamate, and the like. The latter may be used in very small quantities and thus may hereinafter also be called taste-enhancing agents. All the above are suitable to be used alone or as mixtures with other sweeteners and/or flavouring agents. These substances insure great lingering of the sweet taste and cover any undesired aftertaste. Preferred sweeteners and/or taste-enhancing agents include glycosides such as neohesperidin dihydrochalcone. In one embodiment the sweetener of choice may be present in an amount of 0.00001 to 2% (w/w), preferably 0.00001 to 0.1% (w/w), most preferably 0.00001 to 0.001% (w/w), in relation to the total weight of the composition. The taste-enhancing agent of choice may be present in an amount of 0.1 to 50 ppm, preferably 1 to 10 ppm, most preferably 1 to 5 ppm, in relation to the total weight of the composition. Typical flavoring agents include any natural and artificial flavoring agent suitable for pharmaceutical applications, such as flavoring agents derived from a spice, fruit or fruit juice, vegetable or vegetable juice, and the like, for example flavors based on cocoa, caramel, vanilla, apple, apricot, berry (e.g. blackberry, red currant, black currant, strawberry, raspberry, Woodberry, etc.), mint, panettone, honey, nut, malt, cola, verveine (verbena) or any combination thereof, such as for example caramel/vanilla, fruit/cream (e.g. strawberry/cream) and the like. In one embodiment the flavoring agent of choice may be present in an amount of 0.01 to 12% (w/w), preferably 0.1 to 6% (w/w), most preferably 0.1 to 4% (w/w), in relation to the total weight of the composition. Additional examples of useful excipients are described in the Handbook of pharmaceutical excipients, 3rd edition, Edited by A. H. Kibbe, Published by: American Pharmaceutical Association, Washington D.C., ISBN: 0-917330-96-X, or Handbook of Pharmaceutical Excipients ($4^{th}$ edition), Edited by Raymond C Rowe-Publisher: Science and Practice which are incorporated herewith by reference.

Preferably the pharmaceutical composition according to the invention comprises one or more excipients, such as fillers, binders, diluents, lubricants, disintegrants, glidants, disintegrants, coloring agents, flavors, sweeteners, sorbents, stabilizers, surfactants, coating materials or plasticizers, in an amount of at most about 10 wt-%, preferably at most about 5 weight %, more preferably at most about 3 weight %, based on the total weight of the pharmaceutical composition. In a particular preferred embodiment, the pharmaceutical composition according to the invention comprises one or more excipients selected from lubricants and glidants. in an embodiment of the invention the pharmaceutical composition comprises one or more excipients selected from lubricants and glidants in an amount of about 0.5 to about 5 weight % based on the total weight of the pharmaceutical composition. In a particular preferred embodiment, the pharmaceutical composition of the invention comprises:
 a) a mixture of iron(III)-oxyhydroxide, sucrose and one or more starches, preferably sucroferric oxyhydroxide, as defined above,
 b) magnesium stearate,
 c) talc, and
 d) optionally one or more flavours.

Such pharmaceutical composition is particularly suitable for the formation of micro- or mini-tablets, due to a pronounced reduction of ejection forces in microtableting-tools.

Preferably this pharmaceutical comprises at least about 0.5 weight-% of magnesium stearate based on the total weight of the pharmaceutical composition, more preferably about 0.5 to about 1.5 weight-% of magnesium stearate based on the total weight of the pharmaceutical composition. Preferably this pharmaceutical composition comprises at least about 0.5 weight-% talc, more preferably at least 1.0 weight-% based on the total weight of the pharmaceutical composition.

in a further preferred embodiment the pharmaceutical composition comprises about 0.5 to about 1.5 weight-% of magnesium stearate based on the total weight of the pharmaceutical composition and at least about 0.5 weight-% talc, more preferably at least 1.0 weight-% based on the total weight of the pharmaceutical composition, preferably about 0.75 to about 1.25 weight-% of magnesium stearate and about 1.0 to about 3.0 weight-% of talc, each based on the total weight of the pharmaceutical composition.

In a further preferred embodiment of this pharmaceutical composition according to the invention the total amount of magnesium stearate and talc does not exceed 3.0 weight-% based on the total weight of the pharmaceutical composition.

A particularly preferred pharmaceutical composition according to the invention comprises 96 to 98 weight-% of a mixture of iron(III)-oxyhydroxide, sucrose and one or more starches, preferably sucroferric oxyhydroxide, 0.75 to 1.25 weight-% of magnesium stearate and 1.0 to 3.0 weight-% of talc, each based on the overall weight of the pharmaceutical composition, more preferably the pharmaceutical composition according to the invention consists of 96 to 98 weight-% of a mixture of iron(III)-oxyhydroxide, sucrose and one or more starches, preferably sucroferric oxyhydroxide, 0.75 to 1.25 weight-% of magnesium stearate and 1.0 to 3.0 weight-% of talc, each based on the overall weight of the pharmaceutical composition and optionally flavour.

In a preferred embodiment the pharmaceutical composition according to the invention it does not contain any sweeteners. Likewise, in a preferred embodiment the pharmaceutical composition according to the invention does not contain any silica. Likewise, in a preferred embodiment the pharmaceutical composition according to the invention does not contain any flavoring agents. Likewise, in a preferred embodiment the pharmaceutical composition according to the invention does not contain any macrogols. Likewise, in a preferred embodiment the pharmaceutical composition according to the invention does not contain any further excipients apart from magnesium stearate, talc and a flavor.

The pharmaceutical composition according to the invention is in particular for use in the prophylaxis and treatment of hyperphosphataemia conditions, in particular in patients with chronic renal insufficiency. It is thus effective for treating hyperphosphatemia or conditions resulting from unbalanced phosphate levels (e.g. for therapeutic use in the control of serum phosphorous levels in patients with Chronic Kidney Diseases (CKD) who are on dialysis), in view of their ability to adsorb the dietary phosphate in the gastrointestinal tract.

The present invention further relates to a process for the manufacture of a compressed pharmaceutical composition according to the invention, which comprises the step of compressing a non-compressed pharmaceutical composition as defined the bath into a tablet. Such process preferably comprises a step of dry granulating (compaction) of a mixture of iron(III)-oxyhydroxide, sucrose and one or more starches, preferably sucroferric oxyhydroxide prior to compressing the pharmaceutical composition to obtain a compressed tablet. The dry granulation step prior to the compression is preferably effected by roller compaction.

In a preferred embodiment invention relates to a process for the manufacture of a pharmaceutical composition, comprising talc, which process further comprises the steps of sieving the talc, adding the sieved talc to the mixture of iron(III)-oxyhydroxide, sucrose and one or more starches, preferably sucroferric oxyhydroxide, and blending the sieved talc and the mixture of iron(III)-oxyhydroxide, sucrose and one or more starches, preferably sucroferric oxyhydroxide to obtain a preblend. Particularly preferred such process is for the manufacture of a pharmaceutical composition, comprising magnesium stearate, which process further comprises the step of sieving magnesium stearate, mixing the sieved magnesium stearate to a portion of the preblend, comprising talc and a mixture of iron(III)-oxyhydroxide, sucrose and one or more starches, preferably sucroferric oxyhydroxide, and mixing the resulting mixture with the remaining of the preblend to obtain a final blend, which is subjected to compression to obtain a compressed pharmaceutical composition.

The present invention thus further relates to a compressed tablet as obtainable by the process described before, and in particular to a compressed tablet which is a mini- or micro-tablet. Usually such micro- or mini-tablets have diameters between about 1 to 4 mm. Preferably the diameter of the mini- or micro-tablet is in the range of about 1 to 4 mm, more preferably about 1.5 to 3 mm. In a preferred embodiment the compressed mini- or micro-tablet according to the invention as a mass of about 9.1 to about 15.9 mg, preferably about 10.2 to about 14.8 mg, even more preferably from about 11.4 to about 13.6 mg. Preferably the compressed tablet, in particular the micro- or mini-tablets according to the invention have a cylindrical shape, wherein the diameter of the cylinder is preferably in the range of from about 1.7 mm to about 2.3 mm, and wherein the height of the cylinder is preferably in the range of from about 2.5 to about 3.1 mm. The ratio of the diameter to the height of the cylinder of the compressed tablet, in particular the micro- or mini-tablets according to the invention is in the range of from about 0.55 to about 0.92, more preferably in the range from about 0.6 to about 0.8, and most preferably in the range from about 0.65 to about 0.75.

The compressed tablet according to the invention preferably have a mean hardness of the tablet which is in the range from about 5 N to about 25 N determined with a hardness tester following European pharmacopeia monograph 2.9.8.

The compressed tablet according to the invention preferably have a friability of the tablet which is ≤2.0, preferably less ≤1.0% determined with a tablet friability apparatus fitted with an abrasion drum following European pharmacopeia monograph 2.9.7.

The compressed tablet according to the invention have a disintegration time of the tablet which is ≤15 minutes determined with a disintegration apparatus A following European pharmacopeia monograph 2.9.1 (with disc).

A further embodiment of the invention relates to a sachet or a stickpack, containing a plurality of the mini- or micro-tablets as described before. Such sachet or stickpack preferably comprises about 100 to 300, preferably 150 to 250, more preferably 180 to 220 mini- or micro-tablets.

Preferably the sachet or stickpack according to the invention comprises about 500 mg to about 3700 mg of a mixture of iron(III)-oxyhydroxide, sucrose and one or more starches, preferably sucroferric oxyhydroxide, more preferably about 600 mg to about 3600 mg of a mixture of iron(III)-oxyhydroxide, sucrose and one or more starches, preferably sucroferric oxyhydroxide, and further preferably about 800 mg to about 3500 mg of a mixture of iron(III)-oxyhydroxide, sucrose and one or more starches, preferably sucroferric oxyhydroxide, and still further preferably about 1500 mg to about 3500 mg of a mixture of iron(III)-oxyhydroxide, sucrose and one or more starches, preferably sucroferric oxyhydroxide. The sachet or stickpack according to the invention is preferably childsafe for example according to ISO 8317.

The mini- or micro-tablets are preferably provided in a microtablet dose dispenser, such as from the highest technological one to the simplest one: Sensidose®, sMTS®, IQ dose® or homeopathic tube.

In the following the preferred embodiments of the invention are summarized:

1. Particles, comprising iron(III)-oxyhydroxide, sucrose and one or more starches, wherein the fraction of particles with a particle size of above 90 μm is 25 weight % or more, preferably 35 weight % or more, more preferably 40 weight % or more, even more preferably 45 weight % or more, and most preferably 50 weight % or more, and wherein preferably the fraction of particles with a particle size of above 125 μm is 25 weight % or more, more preferably 30 weight % or more, and still more preferably 35 weight % or more, each based on the total weight of the particles, as determined by sieve analysis.

2. Particles according to embodiment 1, wherein the fraction of particles with a particle size in the range of 90 μm to 125 μm is 3 weight % or more, preferably 5 weight % or more, each based on the total weight of the particles, as determined by sieve analysis.

3. Particles according to embodiments 1 or 2, wherein the fraction of particles with a particle size in the range of 125 μm to 180 μm is 3 weight % or more, preferably 5 weight % or more, each based on the total weight of the particles, as determined by sieve analysis.

4. Particles according to any of embodiments 1 to 3, wherein the fraction of particles with a particle size in the range of 180 μm to 250 μm is 3 weight % or more, preferably 5 weight % or more, each based on the total weight of the particles, as determined by sieve analysis.

5. Particles according to any of embodiments 1 to 4, wherein the fraction of particles with a particle size in the range of 250 μm to 355 μm is 3 weight % or more, preferably 5 weight % or more, each based on the total weight of the particles, as determined by sieve analysis.

6. Particles according to any of embodiments 1 to 5, wherein the fraction of particles with a particle size in the range of 355 μm to 500 μm is 3 weight % or more, preferably 5 weight % or more, each based on the total weight of the particles, as determined by sieve analysis.

7. Particles according to any of embodiments 1 to 6, wherein the fraction of particles with a particle size in the range of 500 μm to 710 μm is 3 weight % or more, preferably 5 weight % or more, each based on the total weight of the particles, as determined by sieve analysis.

8. Particles according to any of embodiments 1 to 7, wherein the fraction of particles with a particle size in the range of 90 to 710 μm is 30 weight % or more, preferably 35 weight % or more, each based on the total weight of the particles, as determined by sieve analysis.

9. Particles according to any of embodiments 1 to 8, wherein the fraction of particles with a particle size in the range of 125 μm to 180 μm is 3 weight % or more, preferably 5 weight % or more, the fraction of particles with a particle size in the range of 180 μm to 250 μm is 3 weight % or more, preferably 5 weight % or more, the fraction of particles with a particle size in the range of 250 μm to 355 μm is 3 weight % or more, preferably 5 weight % or more, the fraction of particles with a particle size in the range of 355 μm to 500 μm is 3 weight % or more, preferably 5 weight % or more, and the fraction of particles with a particle size in the range of 500 μm to 710 μm is 3 weight % or more, preferably 5 weight % or more, each based on the total weight of the particles, as determined by sieve analysis.

10. Particles according to any of embodiments 1 to 9, wherein the fraction of particles having a particle size of >710 μm is less than 5 weight %, and preferably less than 3 weight %, based on the total weight of the particles, as determined by sieve analysis.

11. Particles according to any of the previous embodiments 1 to 10, consisting of iron(III)-oxyhydroxide, sucrose, one or more starches and optionally water.

12. Particles according to any of the previous embodiments 1 to 11, which are formed of sucroferric oxyhydroxide.

13. Particles according to any of the previous embodiments 1 to 12, comprising about 20 to about 50 weight % iron (III)-oxyhydroxide, about 20 to 50 weight % sucrose, and about 20 to 50 weight % of one or more starches, based on the total weight of the particles.

14. Particles according to any of the previous embodiments 1 to 13, comprising about 20 to about 40 weight % iron (III)-oxyhydroxide, about 20 to 40 weight % sucrose, and about 20 to 40 weight % of one or more starches, based on the total weight of the particles.

15. Particles according to any of the previous embodiments 1 to 14, comprising about 28 to about 38 weight % iron (III)-oxyhydroxide, about 25 to 35 weight % sucrose, and about 23 to 33 weight % of one or more starches, based on the total weight of the particles.

16. Particles according to any of the previous embodiments 1 to 15, comprising a mixture of native and pregelatinised starch, preferably a mixture of pregelatinised starch and potato starch, preferably having a weight ratio (native: pregelatinized) in the range of 10:1 to 0.5:1, preferably in the range of 3:1 to 0.5:1, more preferably in the range of about 2:1.

17. Particles according to any of the previous embodiments 1 to 16, having an iron content of about 15 to about 28 weight %, preferably about 19 to about 23 weight %, based on the total weight of the particles.

18. Particles according to any of the previous embodiments 1 to 17, comprising water in an amount of up to about 15 weight %, preferably up to about 10 weight %, based on the total weight of the particles.

19. Particles according to any of the previous embodiments 1 to 18, consisting of iron(III)-oxyhydroxide, sucrose, one or more starches and water.

20. Particles according to any of the previous embodiments 1 to 19, consisting of iron(III)-oxyhydroxide, sucrose, a mixture of two or more starches and water.

21. Particles according to any of the previous embodiments 1 to 20, consisting of iron(III)-oxyhydroxide, sucrose, a mixture of native and pregelatinized starch and water.

22. A process for the manufacture of the particles according to any of the previous embodiments, wherein particles, comprising iron(III)-oxyhydroxide, sucrose and one or more starches, wherein the fraction of particles with a particle size of above 90 μm is less than 25 weight %, based on the total weight of the particles, as determined by sieve analysis, are subjected to granulation.

23. A process for the manufacture according to the previous embodiment 22, wherein the particles are subjected to dry or wet granulation, preferred to dry granulation (compaction).

24. A process for the manufacture according to any of the previous embodiments 22 or 23, wherein the particles are subjected to compaction with a roller compactor.

25. A process for the manufacture of the particles according to any of the previous embodiments 22 to 24, wherein the particles, comprising iron(III)-oxyhydroxide, sucrose and one or more starches, wherein the fraction of particles with particle sizes of above 90 μm is less than 25 weight %, are prepared by spray-drying of an aqueous suspension comprising iron(III)-oxyhydroxide, sucrose and one or more starches.

26. Use of particles, comprising iron(III)-oxyhydroxide, sucrose and one or more starches, preferably particles of sucroferric oxyhydroxide, wherein the fraction of particles with a particle size of above 90 μm is 25 weight % or more, preferably 35 weight % or more, more preferably 40 weight % or more, even more preferably 45 weight % or more, and most preferably 50 weight % or more, and wherein the fraction of particles with a particle size of above 125 μm is 25 weight % or more, preferably 30 weight % or more, and more preferably 35 weight % or more, each based on the total weight of the particles, as determined by sieve analysis, for the manufacture of a pharmaceutical composition.

27. A pharmaceutical composition, comprising particles, comprising iron(III)-oxyhydroxide, sucrose and one or more starches, preferably particles of sucroferric oxyhydroxide, wherein the fraction of particles with a particle size of above 90 μm is 25 weight % or more, preferably 35 weight % or more, more preferably 40 weight % or more, even more preferably 45 weight % or more, and most preferably 50 weight % or more, and wherein the fraction of particles with a particle size of above 125 μm is 25 weight % or more, preferably 30 weight % or more, and more preferably 35 weight % or more, each based on the total weight of the particles, as determined by sieve analysis.

28. A compressed pharmaceutical composition, obtainable by compressing a pharmaceutical composition, comprising particles, comprising iron(III)-oxyhydroxide, sucrose and one or more starches, preferably particles of sucroferric oxyhydroxide, wherein the fraction of particles with a particle size of above 90 μm is 25 weight % or more, preferably 35 weight % or more, more preferably 40 weight % or more, even more preferably 45 weight % or more, and most preferably 50 weight % or more, and wherein the fraction of particles with a particle size of above 125 μm is 25 weight % or more, preferably 30 weight % or more, and more preferably 35 weight % or more, each based on the total weight of the particles, as determined by sieve analysis.

29. A compressed pharmaceutical composition according to the previous embodiment 28, which is selected from a tablet, in particular, a mini- or micro-tablet.

30. A pharmaceutical composition according to any of the previous embodiments 27 to 29, comprising at least about 90 wt-%, preferably at least about 95 weight %, still more preferably at least about 97 weight % of the total of iron(III)-oxyhydroxide, sucrose and one or more starches, based on the total weight of the pharmaceutical composition.

31. A pharmaceutical composition according to any of the previous embodiments 27 to 30, comprising at least about 90 wt-%, preferably at least about 95 weight %, still more preferably at least about 97 weight % of sucroferric oxyhydroxide, based on the total weight of the pharmaceutical composition.

32. A pharmaceutical composition according to any of the previous embodiments 27 to 31, comprising one or more excipients, such as fillers, binders, diluents, lubricants, disintegrants, glidants, disintegrants, coloring agents, flavors, sweeteners, sorbents, stabilizers, surfactants, coating materials or plasticizers.

33. A pharmaceutical composition according to any of the previous embodiments 27 to 32, comprising one or more excipients, such as fillers, binders, diluents, lubricants, disintegrants, glidants, disintegrants, coloring agents, flavors, sweeteners, sorbents, stabilizers, surfactants, coating materials or plasticizers, in an amount of at most about 10 wt-%, preferably at most about 5 weight %, more preferably at most about 3 weight %, based on the total weight of the pharmaceutical composition.

34. A pharmaceutical composition according to any of the previous embodiments 27 to 33, comprising one or more excipients selected from lubricants and glidants.

35. A pharmaceutical composition according to any of the previous embodiments 27 to 34, comprising one or more excipients selected from lubricants and glidants in an amount of about 0.5 to about 5 weight % based on the total weight of the pharmaceutical composition.

36. A pharmaceutical composition, according to any of the previous embodiments 27 to 35, comprising:
 a) the particles as defined above,
 b) magnesium stearate
 c) talc, and
 d) optionally one or more flavours.

37. A pharmaceutical composition according to any of the previous embodiments 27 to 36, comprising at least about 0.5 weight-% of magnesium stearate based on the total weight of the pharmaceutical composition.

38. A pharmaceutical composition according to any of the previous embodiments 27 to 37, comprising about 0.5 to about 1.5 weight-% of magnesium stearate based on the total weight of the pharmaceutical composition.

39. A pharmaceutical composition according to any of the previous embodiments 27 to 38, comprising at least about 0.5 weight-% talc, more preferably at least 1.0 weight-% based on the total weight of the pharmaceutical composition.

40. A pharmaceutical composition according to any of the previous embodiments 27 to 39, comprising about 0.5 to about 1.5 weight-% of magnesium stearate based on the total weight of the pharmaceutical composition and at least about 0.5 weight-% talc, more preferably at least 1.0 weight-% based on the total weight of the pharmaceutical composition.

41. A pharmaceutical composition according to any of the previous embodiments 27 to 40, comprising about 0.75 to about 1.25 weight-% of magnesium stearate and about 1.0 to about 3.0 weight-% of talc, each based on the total weight of the pharmaceutical composition.

42. A pharmaceutical composition according to any of the previous embodiments 27 to 41, wherein the total amount of magnesium stearate and talc does not exceed 3.0 weight-% based on the total weight of the pharmaceutical composition.

43. A pharmaceutical composition according to any of the previous embodiments 27 to 42, wherein the composition comprises 96 to 98 weight-% of particles, comprising iron (III)-oxyhydroxide, sucrose and one or more starches, preferably particles of sucroferric oxyhydroxide, 0.75 to 1.25 weight-% of magnesium stearate and 1.0 to 3.0 weight-% of talc, each based on the overall weight of the pharmaceutical composition.

44. A pharmaceutical composition according to any of the previous embodiments 27 to 43, wherein the composition does not contain any sweeteners.

45. A pharmaceutical composition according to any of the previous embodiments 27 to 44, wherein the composition does not contain any silica.

46. A pharmaceutical composition according to any of the previous embodiments 27 to 45, wherein the composition does not contain any flavoring agents.

47. A pharmaceutical composition according to any of the previous embodiments 27 to 46, wherein the composition does not contain any macrogols.

48. A pharmaceutical composition according to any of the previous embodiments 27 to 47, wherein the composition does not contain any further excipients than those indicated before.

49. A pharmaceutical composition according to any of the previous embodiments 27 to 48 for use in the prophylaxis and treatment of hyperphosphataemia conditions, in particular in patients with chronic renal insufficiency.

50. A process for the manufacture of a compressed pharmaceutical composition according to any of the previous embodiments 28 to 49, which comprises the step of compressing a non-compressed pharmaceutical composition as defined in any of the previous embodiments into a tablet.

51. A process for the manufacture of a pharmaceutical composition according to embodiment 50, which comprises a step of dry granulating (compaction) of particles, comprising iron(III)-oxyhydroxide, sucrose and one or more starches, preferably particles of sucroferric oxyhydroxide prior to compressing the pharmaceutical composition to obtain a compressed tablet.

52. A process for the manufacture of a pharmaceutical embodiment according to embodiment 50, wherein the dry granulation step prior to the compression is effected by roller compaction.

53. A process for the manufacture of a pharmaceutical composition, comprising talc, according to any of embodiments 50 to 52, further comprising the step of sieving the talc, adding the sieved talc to the particles, comprising iron(III)-oxyhydroxide, sucrose and one or more starches, preferably the particles of sucroferric oxyhydroxide, and blending the sieved talc and the particles, comprising iron (III)-oxyhydroxide, sucrose and one or more starches, preferably the particles of sucroferric oxyhydroxide to obtain a preblend.

54. The process for the manufacture of a pharmaceutical composition, comprising magnesium stearate, according to embodiment 53, further comprising the step of sieving magnesium stearate, mixing the sieved magnesium stearate to a portion of the preblend and mixing it with the remaining of the preblend to obtain a final blend.

55. A compressed tablet as obtainable by the process according to any of embodiments 50 to 54.

56. A compressed tablet according to embodiment 55, wherein the compressed tablet is mini- or micro-tablet.

57. A compressed mini- or micro-tablet according to embodiment 56, wherein the mass of the tablet is about 9.1 to about 15.9 mg, preferably about 10.2 to about 14.8 mg, even more preferably from about 11.4 to about 13.6 mg.

58. A compressed tablet according to any of embodiments 56 or 57, wherein the tablet has a cylindrical shape.

59. A compressed tablet according to any of embodiments 56 to 58, wherein the diameter of the mini- or micro-tablet is in the range of about 1 to 4 mm, preferably about 1.5 to 3 mm.

60. A compressed tablet according to embodiments 58 or 59, wherein the diameter of the cylinder is in the range of from about 1.7 mm to about 2.3 mm.

61. A compressed tablet according to any of embodiments 58 to 60, wherein the height of the cylinder is in the range of from about 2.5 to about 3.1 mm.

62. A compressed tablet according to any of embodiments 58 to 61, wherein the ratio of the diameter to the height of the cylinder is in the range of from about 0.55 to about 0.92, more preferably in the range from about 0.6 to about 0.8, and most preferably in the range from about 0.65 to about 0.75.

63. A compressed tablet according to any of embodiments 55 to 62, wherein the mean hardness of the tablet is in the range from about 5 N to about 25 N determined with a hardness tester following European pharmacopeia monograph 2.9.8.

64. A compressed tablet according to any of embodiments 55 to 63, wherein the friability of the tablet is 2.0, preferably less 1.0% determined with a tablet friability apparatus fitted with an abrasion drum following European pharmacopeia monograph 2.9.7.

65. A compressed tablet according to any of embodiments 55 to 64, wherein the disintegration time of the tablet is 15 minutes determined with a disintegration apparatus A following European pharmacopeia monograph 2.9.1 (with disc).
66. A sachet or a stickpack, containing a plurality of the mini- or micro-tablets according to any of the embodiments 56 to 65.
67. A sachet or stickpack according to embodiment 66, comprising about 100 to 300, preferably 150 to 250, more preferably 180 to 220 mini- or micro-tablets.
68. A sachet or stickpack according to embodiments 66 or 67, comprising about 500 mg to about 3700 mg of particles, comprising iron(III)-oxyhydroxide, sucrose and one or more starches, preferably particles of sucroferric oxyhydroxide.
69. A sachet or stickpack according to any of embodiments 66 to 68, comprising about 600 mg to about 3600 mg of particles, comprising iron(III)-oxyhydroxide, sucrose and one or more starches, preferably particles of sucroferric oxyhydroxide.
70. A sachet or stickpack according to any of embodiments 66 to 69, comprising about 800 mg to about 3500 mg of particles, comprising iron(III)-oxyhydroxide, sucrose and one or more starches, preferably particles of sucroferric oxyhydroxide.
71. A sachet or stickpack according to any of embodiments 66 to 70, comprising about 1500 mg to about 3500 mg of particles, comprising iron(III)-oxyhydroxide, sucrose and one or more starches, preferably particles of sucroferric oxyhydroxide.
72. A sachet or stickpack according to any of embodiments 66 to 71, wherein the sachet or stickpack is childsafe.

The present invention is further illustrated by the following examples, which shall not be construed to limit the scope of the invention.

EXAMPLES

Comparative Example 1

Figure 2:
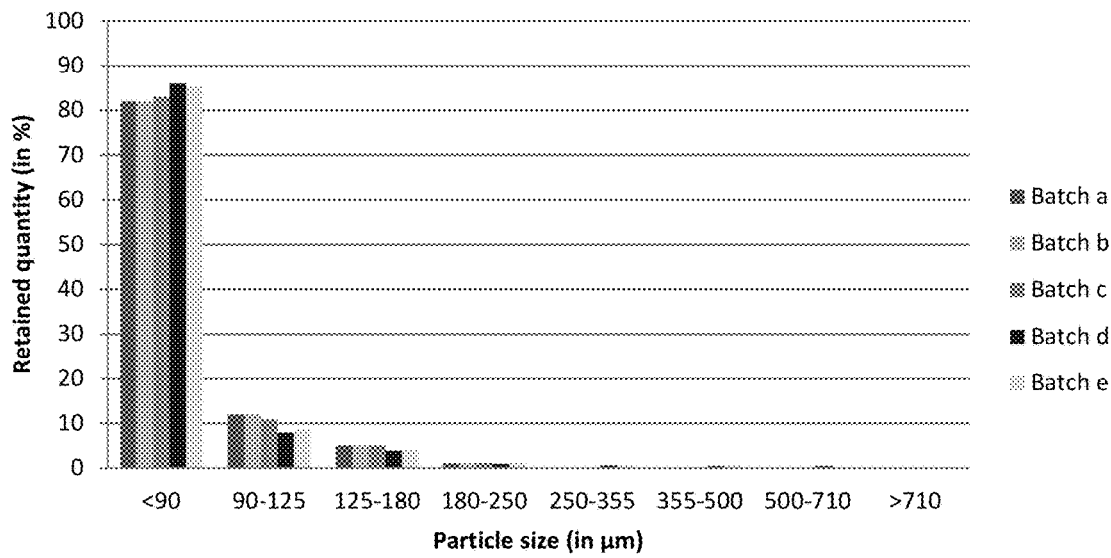
FIG. 2 depicts the particle size as determined by sieve analysis of five batches of a non-compacted sucroferric oxyhydroxide composition according to Comparative Example 1.

Sucroferric oxyhydroxide (a mixture of about 33 wt-% iron(III)oxy hydroxide, about 30 wt-% sucrose, about 28 wt-% starches, and water) was obtained by spray drying as described in WO2008/062993 and WO2015/078900. The sucroferric oxyhydroxide had a particle size where about at least 82 wt-% had a particle size of less than 90 μm as determined by sieve analysis as shown in FIG. 2, which shows the results of five batches. The volume-average particle size d50 as determined by laser diffraction was about 55-56 μm.

Example 1

Sucroferric oxyhydroxide as obtained in comparative example 1 was subjected to roller compaction with a roller compactor (model WP120 from Alexanderwerk) with the following process parameters:

| Process parameter | Settings |
| --- | --- |
| Roller gap | 3.0 mm |
| Hydraulic pressure | 60 bar |
| Sieve size 2 | 0.63 mm |

Figure 3:
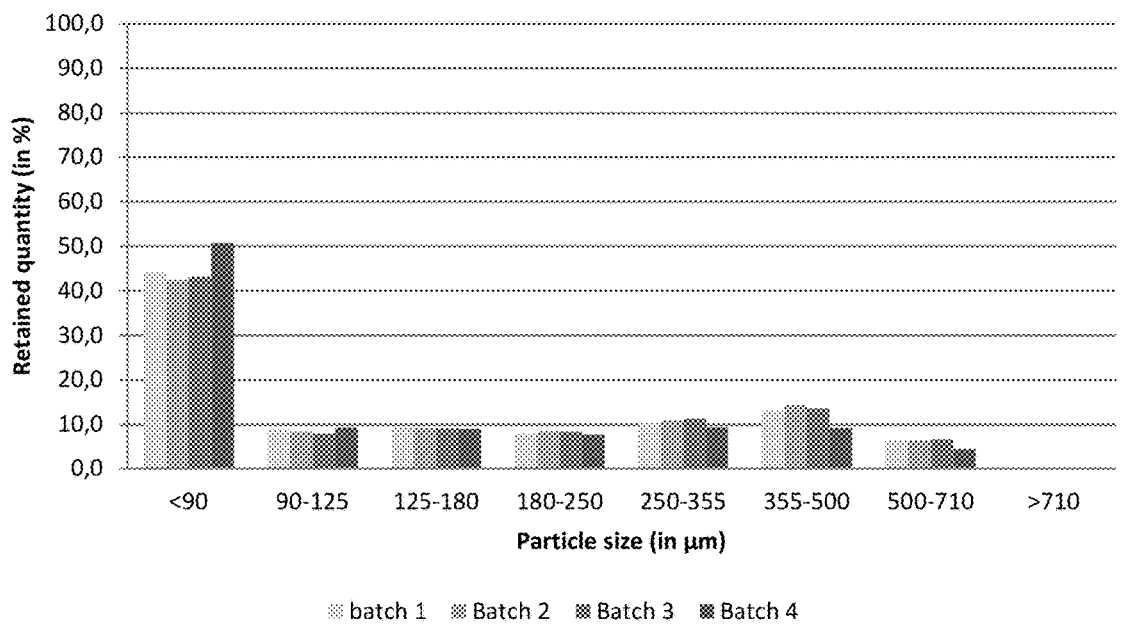
FIG. 3 depicts the particle size as determined by sieve analysis of four batches of an exemplary compacted sucroferric oxyhydroxide composition according to Example 1.

During roller compaction process, the drug substance goes through the roller compactor. The drug substance is compacted in ribbons which are broken with a chopper and then subsequently milled through a final mesh screens size of approx. 0.63 mm. This dry compaction step is implemented to have a coarser particle size distribution of the drug substance. Therefore, the resulting compacted sucroferric oxyhydroxide had a particle size where about 44 wt-% had a particle size of less than 90 μm as determined by sieve analysis as shown in FIG. 3, which shows the results of four batches.

Tableting Examples

Sucroferric oxyhydroxide particles of one batch of each of comparative example 1 and example 1 were each mixed with flavor, sieved talc and sieved magnesium stearate in the quantities shown in the following table (amounts are wt-parts):

| Tableting example | Invention | Comparison |
| --- | --- | --- |
| Compacted sucroferric oxyhydroxide (example 1) | 2500 (equivalent to 500 mg iron) | — |
| Non-compacted sucroferric oxyhydroxide (comparative example 1) | — | 2500 (equivalent to 500 mg iron) |
| Wood berry flavour | 40 | 40 |
| Talc (flow aid/lubricant) | 12.49 | 12.49 |
| Magnesium stearate (lubricant) | 25 | 25 |

Mixing step started with a manual blending of sieved talc with flavor to obtain the pre-blend 1. Then this pre-blend is mixed with one portion of sieved drug substance to obtain the pre-blend 2. The sieved magnesium stearate is added to pre-blend 2 to obtain the pre-blend 3 which was mixed during 5 minutes to obtain the final blend.

The tablet compositions as shown in the table were then each tableted with a rotary tablet press fitted with 16-tips punches, and the ejection force (Multi-tips punches) was recorded. Critical parameters of the tableting process as final compression force or turret speed were fixed in order to achieve the granules (micro-tablets) characteristics regarding hardness, weight, thickness, friability and disintegration time. Red-brown, cylinder shaped granules (micro-tablets) with approximately 2 mm diameter, and approximately 2.8 mm height (thickness) were obtained.

The results on the evolution of the ejection forces are shown in FIG. 1.

The results show a significant lower ejection force (around 300 N lower) for the tablet composition according the invention (compacted sucroferric oxyhydroxide) than for the comparative tablet composition (non-compacted sucroferric oxyhydroxide). Moreover for the tablet composition according the invention the ejection force remains quite stable in time whereas for the comparative tablet composition a slight increase in ejection force. The same trends are observed when the speed of the tableting is increased.

Corresponding to the higher ejection force of the comparative tablet composition tablets made therefrom show dark brown marks on the extremities of the micro-tablets due to heating linked to the higher ejection force, which are not observed with the inventive tablet composition.

The invention claimed is:
1. Particles, comprising iron (III)-oxyhydroxide, sucrose and one or more starches, wherein the fraction of particles with a particle size in the range of 90 μm to 710 μm is 28 weight % or more, wherein the fraction of particles with a particle size in the range of 125 µm to 710 µm is 25 weight % or more, and wherein the fraction of particles with a particle size in the range of 355 µm to 500 µm is 3 weight % or more, each based on the total weight of the particles, as determined by sieve analysis.

2. Particles according to claim 1, wherein the fraction of particles with a particle size in the range of 90 µm to 125 µm is 4 weight % or more, based on the total weight of the particles, as determined by sieve analysis.

3. Particles according to claim 1, wherein the fraction of particles with a particle size in the range of 125 µm to 180 µm is 3 weight % or more, based on the total weight of the particles, as determined by sieve analysis.

4. Particles according to claim 1, wherein the fraction of particles with a particle size in the range of 180 µm to 250 µm is 3 weight % or more, based on the total weight of the particles, as determined by sieve analysis.

5. Particles according to claim 1, wherein the fraction of particles with a particle size in the range of 250 µm to 355 µm is 3 weight % or more, based on the total weight of the particles, as determined by sieve analysis.

6. Particles according to claim 1, wherein the fraction of particles with a particle size in the range of 500 µm to 710 µm is 3 weight % or more, based on the total weight of the particles, as determined by sieve analysis.

7. Particles according to claim 1, wherein the fraction of particles with a particle size in the range of 90 to 710 µm is 30 weight % or more, based on the total weight of the particles, as determined by sieve analysis.

8. Particles according to claim 1, wherein
the fraction of particles with a particle size in the range of 125 µm to 180 µm is 3 weight % or more, and
the fraction of particles with a particle size in the range of 180 µm to 250 µm is 3 weight % or more, and
the fraction of particles with a particle size in the range of 250 µm to 355 µm is 3 weight % or more, and
the fraction of particles with a particle size in the range of 500 µm to 710 µm is 3 weight % or more,
each based on the total weight of the particles, as determined by sieve analysis.

9. Particles according to claim 1, wherein
the fraction of particles with a particle size in the range of 125 µm to 180 µm is at most 20 weight %, and
the fraction of particles with a particle size in the range of 180 µm to 250 µm is at most 20 weight %, and
the fraction of particles with a particle size in the range of 250 µm to 355 µm is at most 20 weight %, and
the fraction of particles with a particle size in the range of 355 µm to 500 µm is at most 20 weight %, and
the fraction of particles with a particle size in the range of 500 µm to 710 µm is at most 20 weight %,
each based on the total weight of the particles, as determined by sieve analysis.

10. Particles according to claim 1, wherein
the fraction of particles with a particle size in the range of 125 µm to 180 µm is in the range of 3 weight % to 20 weight %, and
the fraction of particles with a particle size in the range of 180 µm to 250 µm is in the range of 3 weight % to 20 weight %, and
the fraction of particles with a particle size in the range of 250 µm to 355 µm is in the range of 3 weight % to 20 weight %, and
the fraction of particles with a particle size in the range of 355 µm to 500 µm is in the range of 3 weight % to 20 weight %, and
the fraction of particles with a particle size in the range of 500 µm to 710 µm is in the range of 3 weight % to 20 weight %,
each based on the total weight of the particles, as determined by sieve analysis.

11. Particles according to claim 1, wherein the fraction of particles having a particle size of >710 µm is less than 5 weight %, based on the total weight of the particles, as determined by sieve analysis.

12. Particles according to claim 1 consisting of iron (III)-oxyhydroxide, sucrose, one or more starches and water.

13. The particles of claim 1 made by a process comprising: a) obtaining starting particles, comprising iron (III)-oxyhydroxide, sucrose and one or more starches, wherein the fraction of the starting particles with a particle size in the range of 90 µm to 710 µm is less than 28 weight %, based on the total weight of the starting particles, as determined by sieve analysis and b) subjecting the starting particles to granulation.

14. A pharmaceutical composition, comprising particles, comprising iron (III)-oxyhydroxide, sucrose and one or more starches, wherein the fraction of particles with a particle size in the range of 90 µm to 710 µm is 28 weight % or more, wherein the fraction of particles with a particle size in the range of 125 µm to 710 µm is 25 weight % or more, and wherein the fraction of particles with a particle size in the range of 355 µm to 500 µm is 3 weight % or more, each based on the total weight of the particles, as determined by sieve analysis.

15. A compressed pharmaceutical composition made by a process comprising: a) obtaining a pharmaceutical composition, comprising particles, comprising iron (III)-oxyhydroxide, sucrose and one or more starches, wherein the fraction of particles with a particle size in the range of 90 µm to 710 µm is 28 weight % or more, wherein the fraction of particles with a particle size in the range of 125 µm to 710 µm is 25 weight % or more, and wherein the fraction of particles with a particle size in the range of 355 µm to 500 µm is 3 weight % or more, each based on the total weight of the particles, as determined by sieve analysis and b) compressing the pharmaceutical composition.

16. The compressed pharmaceutical composition according to claim 15, wherein the compressed pharmaceutical composition is a tablet.

17. The compressed pharmaceutical composition according to claim 15, comprising at least about 90 weight % of the total of iron (III)-oxyhydroxide, sucrose and one or more starches, based on the total weight of the compressed pharmaceutical composition.

18. The compressed pharmaceutical composition according to claim 17, further comprising the following excipients:
a) magnesium stearate,
b) talc, and
c) optionally one or more flavours.

19. The compressed pharmaceutical composition according to claim 18, comprising about 0.75 to about 1.25 weight-% of magnesium stearate and about 1.0 to about 3.0 weight-% of talc, each based on the total weight of the pharmaceutical composition.

20. The compressed pharmaceutical composition according to claim 18, wherein the composition does not contain any further excipients.

21. A method of prophylaxis and/or treatment of hyperphosphataemia in a patient with chronic renal insufficiency comprising administering the compressed pharmaceutical composition according to claim 15 to the patient.

22. The compressed pharmaceutical composition according to claim 16, wherein the tablet is a mini-tablet having a mass of about 9.1 to about 15.9 mg.

23. The compressed pharmaceutical composition according to claim 16, wherein the tablet is a mini- or micro-tablet.

24. Particles according to claim 1, wherein the fraction of particles with a particle size in the range of 90 μm to 710 μm is 35 weight % or more, based on the total weight of the particles, as determined by sieve analysis.

25. Particles according to claim 1, wherein the fraction of particles with a particle size in the range of 90 μm to 710 μm is 45 weight % or more, based on the total weight of the particles, as determined by sieve analysis.

26. Particles according to claim 24, wherein the fraction of particles with a particle size in the range of 125 μm to 710 μm is 30 weight % or more, based on the total weight of the particles, as determined by sieve analysis.

27. Particles according to claim 25, wherein the fraction of particles with a particle size in the range of 125 μm to 710 μm is 30 weight % or more, based on the total weight of the particles, as determined by sieve analysis.

28. Particles according to claim 8, wherein the fraction of particles with a particle size in the range of 90 μm to 710 μm is 45 weight % or more, based on the total weight of the particles, as determined by sieve analysis.

29. Particles according to claim 28, wherein the fraction of particles with a particle size in the range of 125 μm to 710 μm is 30 weight % or more, based on the total weight of the particles, as determined by sieve analysis.

30. Particles according to claim 10, wherein the fraction of particles with a particle size in the range of 90 μm to 710 μm is 45 weight % or more, based on the total weight of the particles, as determined by sieve analysis.

31. Particles according to claim 30, wherein the fraction of particles with a particle size in the range of 125 μm to 710 μm is 30 weight % or more, based on the total weight of the particles, as determined by sieve analysis.

32. Particles according to claim 12, wherein the fraction of particles with a particle size in the range of 90 μm to 710 μm is 45 weight % or more, based on the total weight of the particles, as determined by sieve analysis.

33. Particles according to claim 32, wherein the fraction of particles with a particle size in the range of 125 μm to 710 μm is 30 weight % or more, based on the total weight of the particles, as determined by sieve analysis.

34. The pharmaceutical composition according to claim 14, wherein the fraction of particles with a particle size in the range of 90 μm to 710 μm is 35 weight % or more, based on the total weight of the particles, as determined by sieve analysis.

35. The pharmaceutical composition according to claim 14, wherein the fraction of particles with a particle size in the range of 90 μm to 710 μm is 45 weight % or more, based on the total weight of the particles, as determined by sieve analysis.

36. The pharmaceutical composition according to claim 34, wherein the fraction of particles with a particle size in the range of 125 μm to 710 μm is 30 weight % or more, based on the total weight of the particles, as determined by sieve analysis.

37. The pharmaceutical composition according to claim 35, wherein the fraction of particles with a particle size in the range of 125 μm to 710 μm is 30 weight % or more, based on the total weight of the particles, as determined by sieve analysis.

38. The compressed pharmaceutical composition according to claim 15, wherein the pharmaceutical composition obtained in step a) comprises particles, wherein the fraction of particles with a particle size in the range of 90 μm to 710 μm is 35 weight % or more, based on the total weight of the particles, as determined by sieve analysis.

39. The compressed pharmaceutical composition according to claim 15, wherein the pharmaceutical composition obtained in step a) comprises particles, wherein the fraction of particles with a particle size in the range of 90 μm to 710 μm is 45 weight % or more, based on the total weight of the particles, as determined by sieve analysis.

40. The compressed pharmaceutical composition according to claim 38, wherein the pharmaceutical composition obtained in step a) comprises particles, wherein the fraction of particles with a particle size in the range of 125 μm to 710 μm is 30 weight % or more, based on the total weight of the particles, as determined by sieve analysis.

41. The compressed pharmaceutical composition according to claim 39, wherein the pharmaceutical composition obtained in step a) comprises particles, wherein the fraction of particles with a particle size in the range of 125 μm to 710 μm is 30 weight % or more, based on the total weight of the particles, as determined by sieve analysis.

* * * * *